(12) United States Patent
Pfister et al.

(10) Patent No.: US 12,186,142 B2
(45) Date of Patent: Jan. 7, 2025

(54) TORSION-PROTECTION HOUSING FOR GLASS TAG TRANSPONDERS

(71) Applicant: Aesculap AG, Tuttlingen (DE)

(72) Inventors: Ralf Pfister, Trossingen (DE); Frederick Lenzenhuber, Tuttlingen (DE); Stephanie Auber, Tuttlingen (DE); Roland-Alois Hoegerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/282,341

(22) PCT Filed: Mar. 10, 2022

(86) PCT No.: PCT/EP2022/056163
§ 371 (c)(1),
(2) Date: Sep. 15, 2023

(87) PCT Pub. No.: WO2022/194663
PCT Pub. Date: Sep. 22, 2022

(65) Prior Publication Data
US 2024/0180665 A1 Jun. 6, 2024

(30) Foreign Application Priority Data
Mar. 17, 2021 (DE) .................... 10 2021 106 454.6

(51) Int. Cl.
*A61B 90/98* (2016.01)
*G06K 19/077* (2006.01)

(52) U.S. Cl.
CPC ........ *A61B 90/98* (2016.02); *G06K 19/07722* (2013.01)

(58) Field of Classification Search
CPC .......................... A61B 90/98; G06K 19/07722
See application file for complete search history.

(56) References Cited

U.S. PATENT DOCUMENTS

2012/0048947 A1   3/2012  Kube et al.
2016/0128798 A1*  5/2016  Bovet .............. G06K 19/07771
                                                        235/492

FOREIGN PATENT DOCUMENTS

EP     2087850 A2   8/2009
EP     2423855 A1   2/2012
EP     3146477 A1   3/2017
FR     2957240 A1   9/2011
(Continued)

OTHER PUBLICATIONS

Search Report received in International Application No. PCT/EP2022/056163 dated Jun. 28, 2022, with translation, 5 pages.
(Continued)

*Primary Examiner* — Matthew Mikels
(74) *Attorney, Agent, or Firm* — Christopher A. Rothe; CM Law (57) ABSTRACT

A protective housing for accommodating a transponder receivable therein in a medical device. The medical device can be a surgical instrument and/or medical device in a sterilization circuit. The protective housing has at least two integrated snap-in noses on two opposite sides of the protective housing. The snap-in noses are diagonally opposite to each other and formed so as to snap into notches within the medical device in an undercutting manner.

10 Claims, 5 Drawing Sheets

(56) References Cited

FOREIGN PATENT DOCUMENTS

| WO | 2014045265 A1 | 3/2014 |
| WO | 2015177490 A1 | 11/2015 |

OTHER PUBLICATIONS

Written Opinion received in International Application No. PCT/EP2022/056163 dated Jun. 28, 2022, with translation, 13 pages.
Search Report received in German Application No. 10 2021 106 454.6 dated Jan. 25, 2022, with translation, 10 pages.

\* cited by examiner

TORSION-PROTECTION HOUSING FOR GLASS TAG TRANSPONDERS

CROSS-REFERENCE TO RELATED APPLICATIONS

This application is the United States national stage entry of International Application No. PCT/EP2022/056163, filed Mar. 10, 2022, and claims priority to German Application No. 10 2021 106 454.6, filed Mar. 17, 2021. The contents of International Application No. PCT/EP2022/056163 and German Application No. 10 2021 106 454.6 are incorporated by reference herein in their entireties.

FIELD

The present disclosure relates to a protective housing for fastening a transponder receivable therein in/on a medical product, in particular in a surgical instrument and/or medical device in a sterilization circuit. Furthermore, the disclosure relates to a medical system comprising a protective housing and a medical device.

BACKGROUND

Due to the increasing importance in the future of life cycle management of sterile goods, there is an increasing demand for monitoring and traceability of these sterile goods, especially of medical/surgical instruments in a sterilization cycle. For this reason, medical instruments of all kinds are equipped with transponders, especially passive transponders of the RFID-(radio-frequency identification) or NFC (near field communication) technology. This means that the location of the medical instruments can always be identified and a statement can be made as to whether the instruments have passed through the entire reprocessing process or all maintenance steps (correctly). The design of the transponder in the shape of a glass tag is particularly advantageous.

Devices for attaching transponders to medical instruments are already known from the prior art. In document EP 2 087 850, for example, a transponder is attached to a medical instrument with the aid of a housing, e.g. to the handle piece thereof, the housing having a cavity for receiving the transponder. The housing can consist of two separate parts, which enclose the transponder and the instrument handle piece in a recess during a fastening process and can then be connected in a form-fit manner. Another fastening option is to accommodate the transponder in a protective housing that can be folded by way of a hinge and is then strapped to the medical instrument via a flexible strap/belt.

A metallic fastening element for metallic RFID tags is known from EP 3 146 477. The fastening element is attached/adhered to a medical instrument via a flat base area and receives the transponder via a recess enclosed by side surfaces, the transponder and the fastening element being electrically conductively connected to each other, thereby improving the signal strength and the range of the transponder, especially when being fastened to smaller objects.

The attachment of the transponder in accordance with the options indicated above, due to its being fastened to the outside of a medical object and due to protrusions arising therefrom, has an influence on the handling and ergonomics of the retrofitted objects and moreover can make medical processing and cleaning more difficult.

In general, it is also possible to attach a transponder to or in the housing of a medical instrument by bonding/casting/welding or in previously drilled holes. However, those solutions are complex and require appropriate preparations, such as ensuring a clean and grease-free surface of the medical instruments. In addition, pressing the transponder in by force fit or bonding it in place is not permanently enduring due to the settling of plastic.

For accommodating a transponder, e.g. a glass tag protected by a housing, on a medical device, often only small wall thicknesses are available. This means that classic snap elements such as snap-in hooks are hardly feasible due to their necessary dimensions. Moreover, certain instruments such as motor-driven saws are exposed to high vibrations during operation, so that these small size snap elements are too delicate and can break in the long term. So-called ring snap connections, which engage in an instrument housing via a bead have the disadvantage that they exert a force during mounting or engagement due to a deformation of the housing with the transponder accommodated in it, which can destroy the transponder even during assembly.

SUMMARY

Therefore, the present disclosure is based on the task of avoiding or at least mitigating the disadvantages described above. A transponder, in particular a passive RFID tag of the glass tag design, is to be accommodated/fixed in/on a medical device/instrument easily, safely and in a space-saving manner, whereby during the assembly process no or only slight forces are to act directly on the glass tag. Furthermore, it should be possible to rework the medical instruments in a simple manner for the required retrofitting. This type of installation also is to ensure sufficient reliability and reception of the transponder.

Accordingly, the disclosure relates to a protective housing for accommodating/fixing of a transponder receivable therein in/on a medical device, in particular in/on a surgical instrument and/or medical device preferably in a sterilization circuit. The protective housing has on at least two opposite sides at least two integrated, preferably diagonally opposite (i.e. offset from each other in the longitudinal direction of the housing) snap-in noses/bars/protrusions, which are designed to engage in notches/fastening notches/recesses within the medical device in an undercutting manner and the protective housing has recesses respectively opposite the snap-in noses.

In other words, a preferably integrally formed protective housing made of a signal-permeable material, for example of (flexible) plastic, can receive a transponder, in particular an RFID tag in the form of a glass tag, and accommodate this with the aid of at least two snap-in noses/projections/protrusions, which are arranged on at least two opposite sides of the protective housing and are diagonally opposite to each other, in a medical device or in a cavity of the medical device. The medical device has notches/fastening notches/holders in which the snap-in noses of the protective housing engage. The protective housing is fastened by undercutting engagement of the snap-in noses in the notches on the medical device. The protective housing of the transponder is preferably is flat/level/flush with the surface of the medical device.

Preferably, the medical product is a medical device or a medical instrument, a monopolar/bipolar HF instrument, a surgical clamp, surgical forceps, a container, surgical scissors, a scalpel and/or the like. In particular, the medical device may be a motor-driven instrument with a handpiece, wherein the motor may be integrated, and/or a tool, which can be coupled to the handpiece in an engaging manner.

Accordingly, it is safeguarded that the transponder can be accommodated in/on medical device securely and in a space-saving manner, as the configuration of the protective housing does not have any delicate protruding elements. This mounting method allows to dispense with a costly surface preparation process of the medical device, which would be necessary, for example, if the transponder were attached by gluing or welding. A further advantage is that the notches on the instrument housing can be applied relatively easily and inexpensively by postprocessing or already during the manufacturing process.

According to an advantageous embodiment, the snap-in noses of the protective housing are formed such that they engage in the notches within a groove formed on the housing of the medical device in an undercutting manner.

In other words, the housing of the medical device has a groove or recess into which the protective housing (with the transponder) is inserted. In particular, the shape and the depth of the groove can be adapted to the dimensions of the protective housing in such a way that the protective housing, in its attached/mounted state, is completely surrounded by the groove and its surface seamlessly adjoins that of the medical instrument, or is even (slightly) set back. The decisive factor here is that the protective housing preferably does not protrude beyond the surface of the medical device. In this case, the notches that receive the snap-in noses of the protective housing are arranged or formed in the groove of the medical device.

This ensures that the protective housing with the received transponder can be accommodated entirely in the instrument housing, thus counteracting protrusion of the protective housing from the surface of the medical device. This leads to better handling and simplifies the cleaning process as well as storage of the medical device. At the same time, this design with a groove on the housing of the medical device likewise is possible by way of comparatively simple postprocessing or a simple manufacturing process.

The protective housing (also additionally) has recesses in each case opposite to the snap-in noses, i.e. each snap-in nose on one side of the housing is respectively associated with a recess on the side of the housing facing away from it.

According to a further advantageous embodiment, the recesses of the protective housing create maneuvering spaces within the limits of which the protective housing is twistable or deflectable along its longitudinal axis during assembly.

Therefore, if snap-in noses each are arranged on both sides of the housing (facing away from each other), the two housing sides (facing away from each other) each also have the same number of recesses, each of which is opposite to one of the snap-in noses (for example, alternately or only once). In this way it can be achieved that the protective housing during assembly, i.e. during insertion of the housing-side snap-in nose as a first assembly step, followed by an insertion of the housing-side recess as a second assembly step, can twist or deflect in its longitudinal axis or torsion axis. The snap-in noses/latching elements of the protective housing deflect elastically inwards on account of such a torsional movement, i.e. in a direction opposite to the housing of the medical device. As soon as all the snap-in noses have been inserted into the respectively provided notches on the housing of the medical device, or have snapped/latched into the respectively provided notches, the protective housing is fastened to the housing of the medical device in an undercutting manner.

In other words, there are recesses on the side surfaces of the protective housing, on which the snap-in noses (also) are formed. One of the recesses each is directly opposite one of the snap-in noses, which is on the opposite side. When mounting the protective housing, the snap-in noses can be accommodated unhindered by the notches on the housing of the medical device, as the protective housing can escape into them through the recess on the opposite side by a small distance, until the snap-in nose finally engages in the notch and the protective housing again snaps back by the escaped distance. Due to the fact that the protective housing has at least two diagonally opposite snap-in noses, the protective housing during mounting on the medical device can serve as a twisting snap element in its longitudinal axis/main axis.

According to another advantageous aspect of the disclosure, the snap-in noses (on two opposite sides of the protective housing) are offset from one another along the longitudinal axis of the protective housing. In other words, the at least two snap-in noses on the two opposite sides of the protective housing are arranged asymmetrically or alternately with respect to one another, so that when the snap-in noses are snapped/engaged in the corresponding notches on the medical device, a torsional force is generated.

Furthermore, during assembly, the protective housing can twist or deflect in its longitudinal axis by recesses within the groove, which each are formed opposite the snap-in noses. This means that in this embodiment, the recesses are not located directly on the protective housing of the transponder, but are formed or arranged within the groove on the housing of the medical device. The mode of operation of the recesses in this embodiment is similar to the recesses that are formed directly on the protective housing.

Due to this torsion mounting principle of the protective housing there is no risk that the protective housing detaches or winds itself out of the notches in the medical device due to forces caused by vibrations/oscillations that occur during the operating state of the medical device, in particular of a motor-driven medical instrument.

The protective housing can further accommodate the transponder in a bore along the longitudinal axis of the protective housing. For example, the transponder is located centrally in the protective housing and is fully surrounded by the protective housing lengthwise.

Thus, the entire circumference of the transponder can be adequately protected from the forces during assembly of the protective housing or during operation of the medical device. In addition, the possibility of accommodation, in the form of a borehole, requires little manufacturing effort of the protective housing.

The disclosure further relates to a transponder system with a protective housing having a transponder accommodated therein, the transponder is being surrounded, in addition to the protective housing, by a flexible protective layer, which is thereby located between the transponder and the protective housing.

In the assembled state, the protective layer serves as a damping unit between the transponder and the protective housing. Before the transponder is accommodated in the protective housing, it is additionally fully surrounded by a flexible protective layer, for example a silicone layer. The transponder, including the protective layer, has somewhat larger dimensions than the reception in the protective housing, in particular in the form of a bore, whereby the flexible material of the protective layer is compressed during the process of accommodating the transponder in the protective housing. Accordingly, any possible clearance between the transponder and the protective housing is prevented.

A preferred embodiment with an additional protective layer as a damping between the transponder and the protective housing offers a further possibility of increasing the safety of the transponder against extreme vibrations and oscillations in the operating state.

The execution of a protective housing which can be separated again from the medical device, enables medical instruments to be replaced or exchanged without the attached/mounted transponder including the protective housing needing to be exchanged. In certain cases, removal of the transponder can also create the possibility of reassignment, since the protective housing including the transponder can be inserted into a medical object of a different type.

Further preferably, the protective housing has a metal housing in addition to the protective housing.

In other words, the protective housing is integrated in the medical device with an additional metal housing. This is especially necessary if the medical device has a signal-permeable housing made of plastic. In this case, the additional metal housing acts as a signal reflector for the signals of the transponder. This signal amplification ensures sufficient receptivity and reliability.

The disclosure further relates to a medical system preferably comprising the medical device as described above, and the protective housing described above. The snap-in noses of the protective housing snap in notches within a groove formed on the housing of the medical device in an undercutting manner and the protective housing during assembly is twistable or deflectable along its longitudinal axis by way of recesses within the groove respectively formed opposite to the snap-in noses and/or by way of recesses on the protective housing respectively opposite the snap-in noses.

In a preferred embodiment, the snap-in noses of the medical system are configured so that the protective housing is not detachable from the medical device after the assembly.

In another preferred alternative embodiment, the snap-in noses of the medical system are configured so that the protective housing is detachable from the medical device after the assembly.

In other words, the snap-in noses of the protective housing of the medical system on the one hand can be designed in such a way that after anchoring in the notches provided in the medical protective housing, they no longer are to be detached. On the other hand, the shape of the snap-in noses can also be designed such that the protective housing can be separated again from the medical device by actuation on the part of a user.

Therefore, the medical system is configured such that the protective housing can be twisted or deflected in its longitudinal axis during assembly through recesses within the groove of the medical device, which each are formed opposite to the snap-in noses. In other words, the recesses, which each are arranged opposite to a snap-in nose, are not formed directly on the protective housing, but within the groove of the medical device. Such an arrangement of the recesses, too, allows a twisting of the protective housing during assembly, so that the snap-in noses can evade elastically inwards and can thus be snapped in the corresponding notches on the medical device.

Preferably, the groove of the medical system comprises additional material recesses, so that in the assembled state of the protective housing, cavities are formed between the protective housing and the medical device, which are accessible from the bottom side of the protective housing or from the inside.

In other words, the housing of the medical device/object, on the groove formed on it, preferably on the base surface of the groove, has additional material recesses in particular on the sides along the longitudinal axis of the protective housing. In the assembled state of the protective housing, these material recesses form advantageous cavities/gaps between the two components.

Due to these cavities, which are accessible from the bottom side of the protective housing or from the inside, it is difficult for particles or other unwanted substances to deposit between the protective housing and the medical product. At the same time, the cavities are easily/simply accessible for cleaning procedures, which ensures that the medical instruments can always be reprocessed medically in accordance with cleaning requirements.

BRIEF DESCRIPTION OF THE DRAWINGS

The disclosed subject matter will now be illustrated in more detail by means of advantageous embodiments and with reference to the corresponding figures. The figures are merely schematic in nature and exclusively serve for understanding the invention. It is pointed out to the fact that the features of the individual embodiments can be interchanged and can occur in any combination.

DETAILED DESCRIPTION

In the following, the present disclosure as well as the advantageous embodiments are described with reference to the figures.

Figure 1:
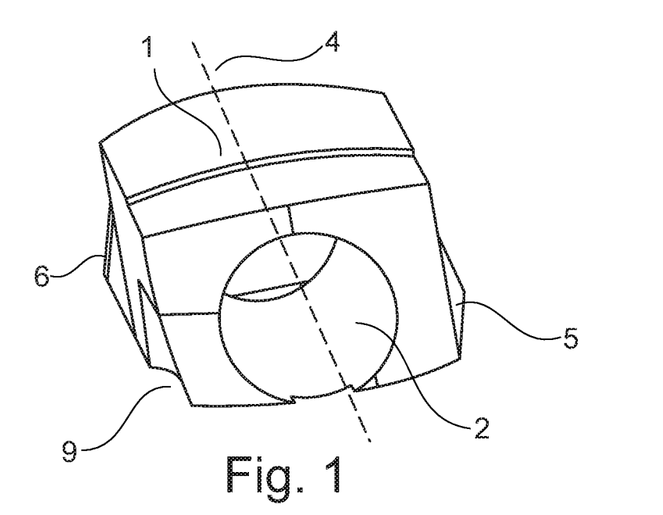
FIG. 1 is a front view of the protective housing for a transponder according to the invention.

FIG. 1 is a representation illustrating the protective housing 1 according to the invention with a longitudinal axis 4. The protective housing 1 is of elongate shape and has a circular (through) hole 2 along the longitudinal axis 4 for receiving a transponder 3. According to the invention snap-in noses 5, 6 are respectively formed on two side surfaces of the protective housing 1 which face away from each other and are essentially parallel to each other and which also run parallel to the hole 2, which snap-in noses extend outwards from the respective side surface. A first snap-in nose 5 is formed on a longitudinal end portion of the protective housing 1 on one side surface, while a second snap-in nose 6 is formed on the other longitudinal end portion on the other the other side surface facing away such that the two snap-in noses 5, 6 are diagonally opposite to each other (with respect to the housing). In addition, the protective housing 1 also has recesses 8, 9 on the two side surfaces facing away from each other, which each are located opposite the snap-in noses 5, 6 of the respective other side surface.

Figure 2:
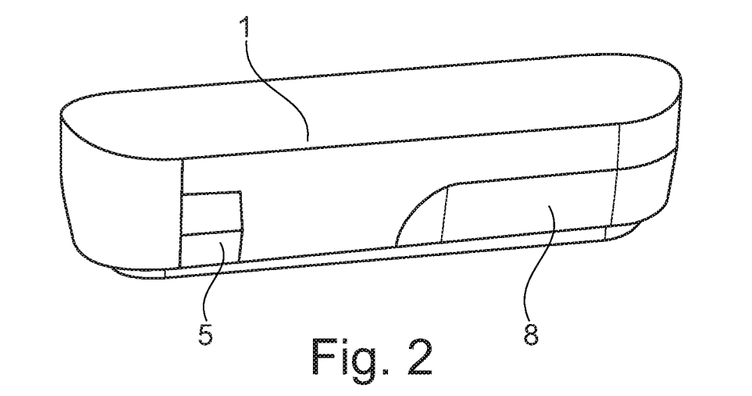
FIG. 2 is a side view of the protective housing for a transponder according to the invention.

FIG. 2 is another illustration of the protective housing 1 from a side view.

The respective ends (end portions) of the protective housing 1 are convexly rounded. The one lateral snap-in nose 5 shown in FIG. 2 here is located on the left end (end portion) of the protective housing 1, the elongated recess 8 being located at the right end (end portion). The recess 8 is formed such that it extends along the longitudinal axis 4 of the protective housing 1 from one end to approximately the middle, at which point the recess 8 curves into the original side surface. The recess 9 (confer FIG. 1) is formed on the opposite side surface of the protective housing 1 and is located diagonally opposite the recess 8.

Figure 3:
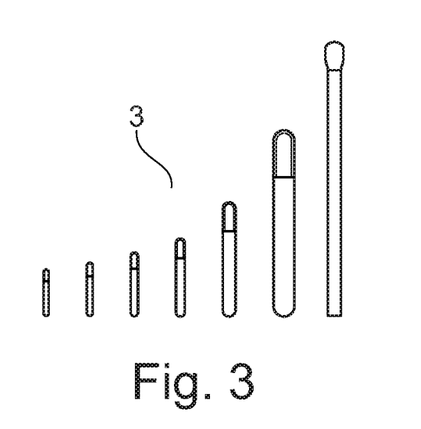
FIG. 3 is a representation illustrating the dimensions of a glass tag transponder.

FIG. 3 is an illustration of transponders that can be utilized according to the invention. The transponders can be configured in particular as passive RFID transponders, an advantageous design being that of a glass tag 3. The execution of the glass tag 3 has a pill-like shape and has a circular cross-sectional area as well as rounded ends. In FIG. 3, different sizes of the glass tag 3 are compared to a commercially available match in order to illustrate the dimension of the transponders. Glass tags 3 of this type are essentially part of the prior art, so that no further description is required.

Figure 4:
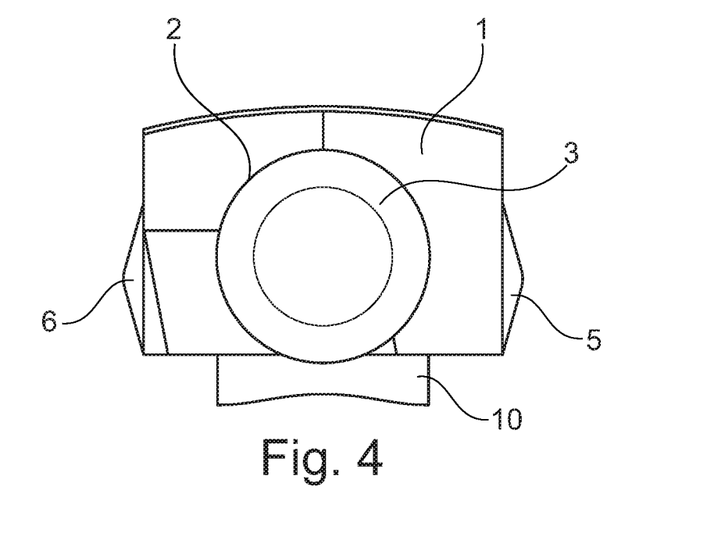
FIG. 4 is a front view of the protective housing according to the invention with a glass tag received therein.

FIG. 4 is a front view of the protective housing 1 according to the invention with a transponder accommodated therein in the design of a glass tag 3. The hole 2 along the longitudinal axis 4 of the protective housing 1 has a diameter adapted to the glass tag 3, so that the latter can be received fully and precisely fitting by the hole 2 over its circumference. Moreover, the length of the protective housing 1 is adapted to the length of the glass tag 3 such that the ends of the glass tag 3 do not protrude from the protective housing 1. Furthermore, the base surface of the protective housing 1 has an additional cuboidal portion 10, which protrudes and is rounded on the bottom side. The snap-in noses 5, 6 on the side surfaces of the protective housing 1 that are respectively diagonally opposite to each other have triangular cross-sectional areas, which are axis-symmetrical with respect to a horizontal center line.

Figure 5:
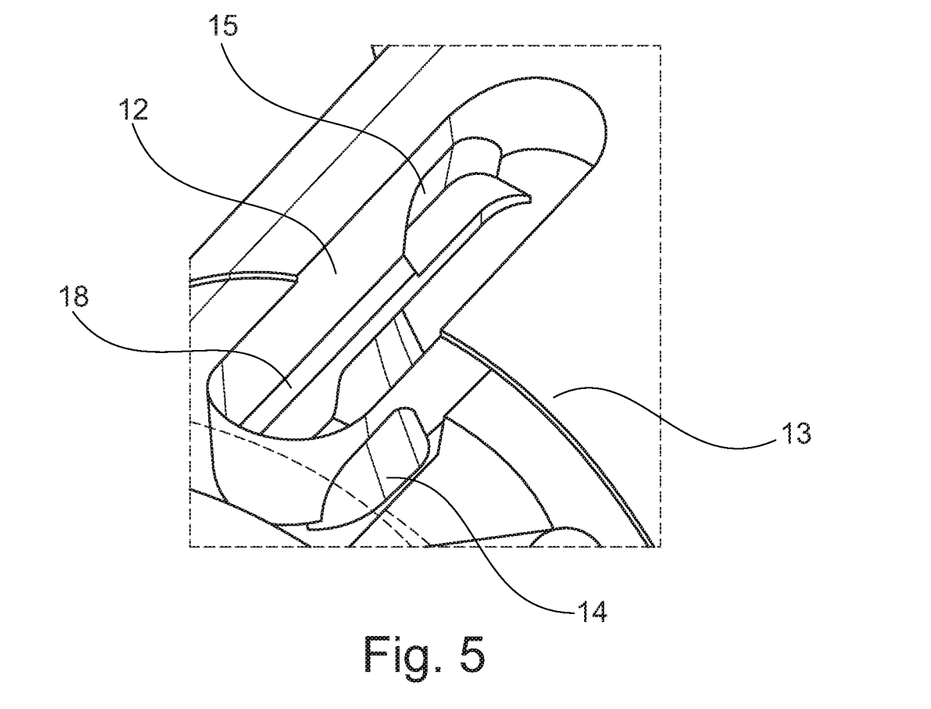
FIG. 5 is an illustration of the groove on the housing of a medical instrument for receiving the protective housing according to the invention.

FIG. 5 shows a groove 12, which is formed/arranged on the surface or housing of a medical instrument 13 and which is adapted to the shape of the protective housing 1 according to the present invention (with a glass tag 3 received therein). Here, the groove 12 can be fitted during the manufacturing process of the instrument 13 or also during an additional post-processing process of the surface, for example by means of a milling process. In this advantageous embodiment, the groove 12 has a so-called stadium shape, i.e. a shape formed by a rectangle with two adjacent semicircles. Notches 14, 15 are formed laterally within the groove 12, the positions of which are respectively aligned with the snap-in noses 5, 6 according to the invention. Thus, these notches 14, 15 likewise are diagonally opposite one another within the groove 12. Furthermore, elongate projections 17, 18 are formed along the two longitudinal sides of the groove 12, against which the protective housing 1 can rest in the assembled state.

Figure 6:
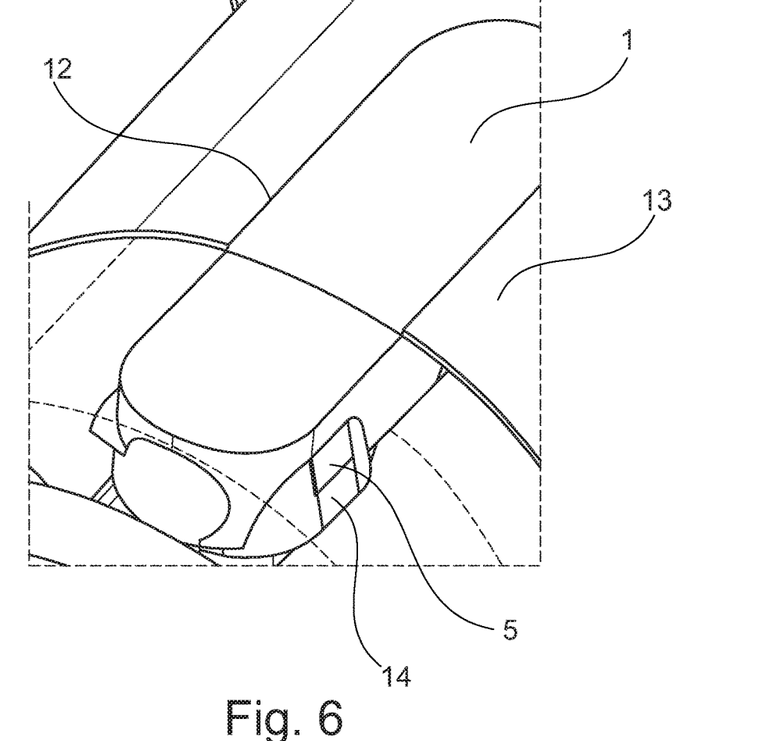
FIG. 6 is an illustration of the groove on the housing of a medical instrument with a protective housing accommodated therein.

FIG. 6 is a representation illustrating the protective housing 1 (with the glass tag 3 accommodated therein) in an assembled state. Here, the protective housing 1 is accommodated within the groove 12 on/in the medical instrument 13, the depth of the groove 12 being aligned to the height of the protective housing 1 according to the invention such that the upper side of the protective housing 1 is on the same level as the surface of the instrument, or is (slightly) offset, which is why the surface of the instrument 13 is not impaired. In this advantageous embodiment, the size of the groove 12 is adapted to the protective housing 1, so that in the assembled state there is no clearance between the protective housing 1 and the housing of the medical instrument 13. In this view, the snap-in nose is received by the notch 14 and is in the engaged state.

Figure 7:
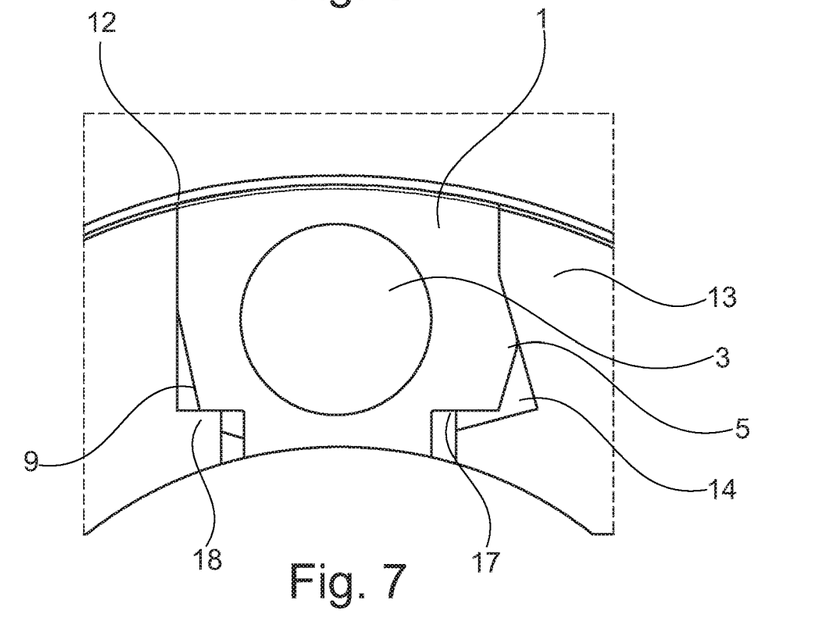
FIG. 7 is a sectional view through the medical instrument and the assembled protective housing with glass tag.

FIG. 7 shows a sectional view perpendicular to the longitudinal axis 4 of the protective housing 1, which runs through the groove 12 in the instrument housing with the protective housing according to the invention accommodated therein. The protective housing 1 has a glass tag 3 in its hole 2. The cutting plane runs at the height of snap-in nose 5 and the opposite recess 9 on the protective housing 1 as well as the associated notch 14 in the groove of the medical instrument 13, i.e., through the front half of the protective housing 1. The cross-section of the notch 14 in the groove 12 for receiving the snap-in nose 5 of the protective housing 1 is formed so that the upper half of the snap-in nose 5 abuts the notch 14 and is received in an undercutting manner. At the same time, there is a clearance between the medical instrument 13 and the lower half of the snap-in nose 5, both on the side and on the bottom side of the snap-in nose 5, which corresponds to the base surface of the protective housing 1. Due to the recess 9 and the previously described clearance between the snap-in nose 5 and the medical instrument 13, this half of the protective housing 1 can be twisted during the assembly process during the assembly process with respect to an axis that protrudes vertically from the sectional plane (in a clockwise direction as shown in FIG. 7). Only through this twisting movement can the snap-in nose 5 of the protective housing 1 according to the invention be received by the notch 14 within the groove 12 in an undercutting manner. The recess 8, notch 15 and snap-in nose 6 in the second cross-sectional plane, which runs through the rear half of the protective housing 1, have the same function as their respective diagonally opposite counterparts, whereby the rear half of the protective housing 1 can twist counterclockwise. The base surface of the protective housing 1, apart from the points where the snap-in noses 5, 6 are formed, abuts projections 17, 18 of the instrument housing. Through these projections 17, 18 and the undercutting engagement of the snap-in noses 5, 6 in the notches 14, 15, the protective housing 1 is fixed vertically.

Figure 8:
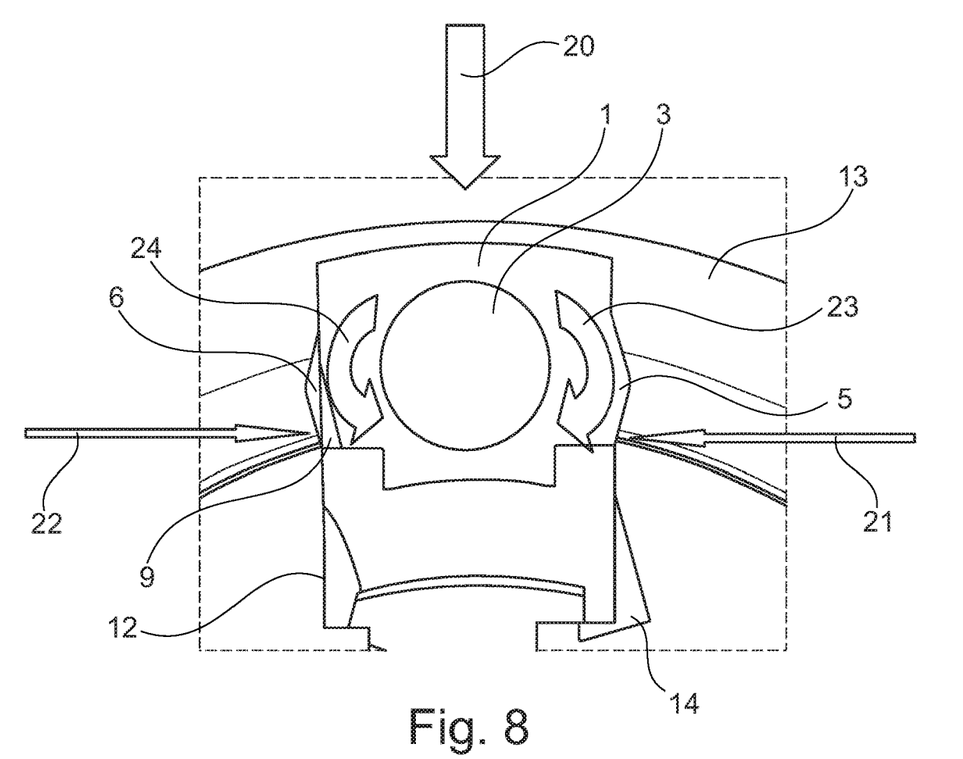
FIG. 8 is a sectional view of the protective housing during assembly on a medical instrument with the forces and moments that occur.
Figure 9:
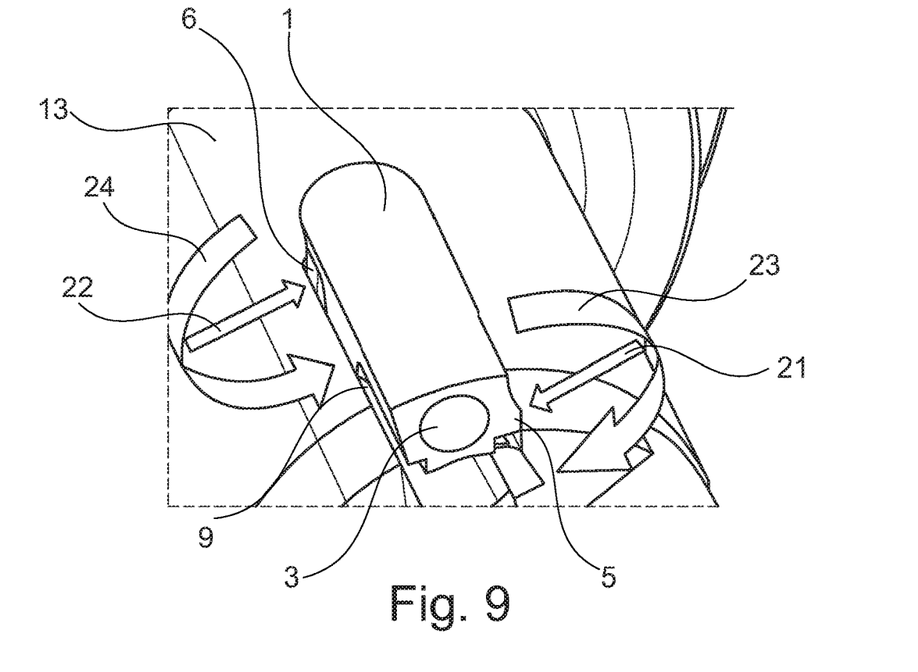
FIG. 9 is a top view onto the protective housing during the assembly process on a medical instrument, with the forces and moments that occur.

FIGS. 8 and 9 each show the protective housing 1 cut through the plane of front snap-in nose 5 with a glass tag 3 received therein during an assembly process into the medical instrument 13. In addition, the forces 20, 21, 22 and moments 23, 24 are marked which act on the protective housing 1 during the assembly process. FIG. 8 shows a sectional view and FIG. 9 a top view. To accommodate or engage the protective housing 1 in the groove 12 provided in the medical instrument 13, a mounting force 20 acts vertically on the protective housing 1, causing the protective housing 1 including the glass tag 3 to be pressed into the groove 12 of the medical instrument 13. During this process, horizontal latching forces 21, 22 act on the front and rear snap-in noses 5, 6 through the instrument housing on the sides of the protective housing 1. A torsional moment 23 (clockwise according to FIGS. 8 and 9) in the front half of the protective housing 1 and a counter torsional moment 24 (counterclockwise) in the rear half of the protective housing 1 represent the movement capacities during the engagement process, which result from the afore-described recesses 8, 9 and the shape of the notches 14, 15 in the groove 12.

Figure 10:
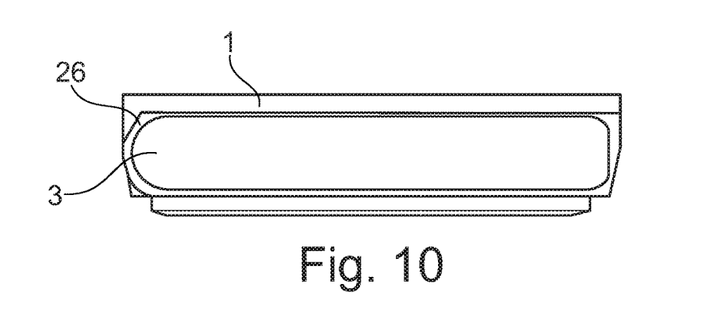
FIG. 10 is a sectional view along the longitudinal axis of the protective housing and the glass tag received therein with an additional protective layer.

FIG. 10 is a sectional view along the longitudinal axis 4 of the protective housing 1 according to the invention with a glass tag 3 which is completely accommodated in the (through) hole 2. The entire glass tag 3 is enclosed by a flexible protective layer 26 to protect it from increased vibrations and oscillations. The thickness of the protective layer 26 is selected such that, when the glass tag 3 is inserted into the hole 2 of the protective housing 1, the protective layer 26 is compressed. Thus, when the glass tag 3 is mounted, there is no clearance between the glass tag and the surrounding protective housing 1, whereby unintentional detachment/slipping through is prevented.

Figure 11:
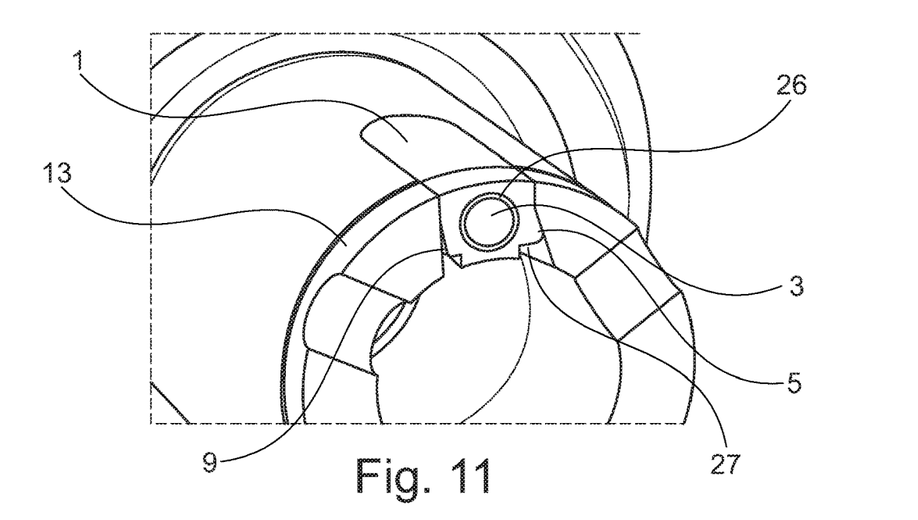
FIG. 11 is a sectional view of the protective housing with a glass tag accommodated in a medical instrument with additional material recesses.
Figure 12:
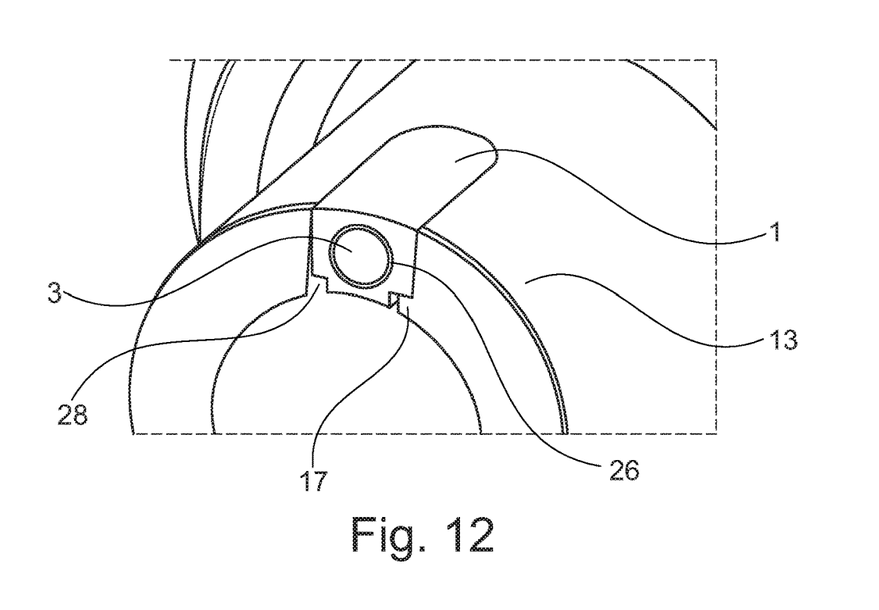
FIG. 12 is a further sectional view of the protective housing with a glass tag accommodated in a medical instrument with additional material recesses.

FIGS. 11 and 12 show a sectional view of a further advantageous embodiment of the medical instrument 13 with an accommodated glass tag 3 in a protective housing 1. The lateral projections 17, 18 in the groove 12 of the medical instrument 13, which serve for vertical fixation of the protective housing 1, are not continuous and partially have material recesses 27, 28. Preferably, those recesses are located below the snap-in noses 5, 6 and recesses 8, 9 of the protective housing 1. This results in cavities accessible from the inside/from inside (of the medical device), which facilitate easier cleaning when the protective housing 1 is in the installed state. At the same time, vertical fixation can be safeguarded by the projections 17, 18 on the remaining portions of the bottom side of the protective housing 1. This advantageous embodiment may have a protective layer 26 between the glass tag 3 and the protective housing 1 or not.

The invention claimed is:

1. A protective housing for accommodating a transponder receivable in the protective housing in a medical device,
    the protective housing comprising a longitudinal axis and at least two snap-in noses diagonally opposite to each other and formed so as to engage in notches within the medical device in an undercutting manner, and
    the protective housing comprising recesses respectively opposite the snap-in noses.

2. The protective housing according to claim 1, wherein the recesses create maneuvering spaces, and wherein the protective housing is twistable or deflectable along the longitudinal axis during assembly within the maneuvering spaces.

3. The protective housing according to claim 2, wherein the snap-in noses are offset from one another along the longitudinal axis of the protective housing.

4. The protective housing according to claim 1, wherein the protective housing receives the transponder in a hole along the longitudinal axis of the protective housing.

5. A transponder system comprising:
    the protective housing according to claim 1; and
    a transponder accommodated in the transponder housing, wherein the transponder is surrounded by a flexible protective layer located between the transponder and the protective housing.

6. The protective housing according to claim 1, wherein the protective housing further comprises a metal housing.

7. A medical system comprising:
    the protective housing according to claim 1; and
    a medical device comprising a housing,
    wherein the at least two snap-in noses of the protective housing snap in notches within a groove formed on the housing of the medical device in an undercutting manner and the protective housing during assembly is twistable or deflectable along the longitudinal axis by way of recesses within the groove respectively formed opposite to the at least two snap-in noses and/or by way of recesses on the protective housing respectively opposite the at least two snap-in noses.

8. The medical system according to claim 7, wherein the groove has additional material recesses formed in such a way that in the mounted state of the protective housing, cavities that are accessible from its bottom side are formed between the protective housing and the medical device.

9. The medical system according to claim 7, wherein the at least two snap-in noses are configured so that the protective housing is not detachable from the medical device after assembly.

10. The medical system according to claim 7, wherein the at least two snap-in noses are configured so that the protective housing is detachable from the medical device after assembly.

* * * * *